United States Patent [19]

Mashovsky et al.

[11] Patent Number: 5,326,774
[45] Date of Patent: Jul. 5, 1994

[54] PHARMACEUTICAL PREPARATION OF ANTIHYPERTENSIVE, ANTIANGINAL, ANTIARRHYTHMIC AND ANTIGLAUCOMIC ACTION

[76] Inventors: Mikhail D. Mashovsky, Leningradsky prospekt, 57-A, kv. 55; Sergei D. Juzhakov, ulitsa Ostrovityanova, 26, korpus 2, kv. 32; Leonid V. Rozenshtraukh, ulitsa Osennaya, 2, kv. 27; Oleg S. Medvedev, Berezhkovskaya naberezhnaya, 14, kv. 32; Evgeny P. Anjukhovsky, ulitsa Osennaya, 2, kv. 4; Elena V. Dorodnikova, ulitsa Garibaldi, 27, korpus 3, kv. 47; Olga V. Dolgun, ulitsa Pyrieva, 5, korpus 5, kv. 187; Aron Y. Bunin, Verkhny Mikhailovsky proezd, 10, kv. 155; Valentina N. Ermakova, Volzhsky bulvar, 20, kv. 148, all of Moscow; Vladimir I. Metelitsa, Jubileiny prospekt, 35, kv. 186, Moskovskaya oblast Khimki; Vladimir K. Piotrovsky, prospekt Mira, 184, kv. 184, Moscow, all of Russian Federation

[21] Appl. No.: 928,046

[22] Filed: Aug. 11, 1992

[51] Int. Cl.$^5$ .................... C07D 413/12; A61K 31/42
[52] U.S. Cl. .................... 524/361; 514/821; 514/913; 548/131
[58] Field of Search .......... 548/131; 514/361, 821, 514/913

[56] References Cited

U.S. PATENT DOCUMENTS

| | | | |
|---|---|---|---|
| 3,862,168 | 1/1975 | Findeisen et al. | 548/131 |
| 4,096,273 | 6/1978 | Gutman | 548/131 X |
| 4,294,843 | 10/1981 | Weston | 548/131 X |
| 4,500,340 | 2/1985 | Becker et al. | 548/131 X |
| 4,753,671 | 6/1988 | Someya et al. | 548/131 X |

OTHER PUBLICATIONS

Angina Pectoris: After Nitrates and beta-blockers what next? H. B. Kay, Alfred Hospital, Melbourne, Australia (Nov. 1981).

McDevitt D. G., Adrenoceptor blocking drugs: clinical pharmacology and therapeutic use, Drugs, 1979, pp. 267–288.

Louis W. J., McNeil J. J., Drummer O. H., Pharmacology of Combined α, β-blockade, Drugs, 1984, 28, suppl. 2, pp. 17–33.

*Primary Examiner*—Marianne M. Cintins
*Assistant Examiner*—Catherine S. Kilby Scalzo
*Attorney, Agent, or Firm*—Jacobson, Price, Holman & Stern

[57] ABSTRACT

An antihypertensive, antianginal, antiarrhythmic and antiglaucomic pharamaceutical preparation consists of an active principle, namely 3-methyl-5-[2-(3-tert.-butylamino-2-hydroxypropoxy-phenoxymethyl]-1,2,4-oxadiazole hydrochloride of the following formula:

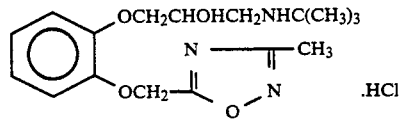

and a pharmaceutically acceptable diluent.

6 Claims, No Drawings

PHARMACEUTICAL PREPARATION OF ANTIHYPERTENSIVE, ANTIANGINAL, ANTIARRHYTHMIC AND ANTIGLAUCOMIC ACTION

FIELD OF THE INVENTION

The present invention relates to medicine, and more particularly it relates to novel pharmaceutical preparation having an antihypertensive, antianginal antiarrhythmic and antiglaucomic action which is used in cardiological practice in case of arterial hypertension, heart ischemia, supraventricular and ventricular tachyarrhythmias, as well as in ophthalmology for decreasing an intraocular tension in primary open-angle glaucoma at different stages of such disease and with different degree of increasing the intraocular tension, in secondary glaucoma, and in angle-closure glaucoma.

BACKGROUND OF THE INVENTION

Nowadays, $\beta$-adrenoceptor blocking agents are in widespread use in therapy as medicinal agents for the most prevalent cardiovascular diseases such as arterial hypertension, heart ischemia, as well as for the treatment of arrhythmias.

However, despite quite a wide nomenclature of $\beta$-adrenoceptor blocking compounds which are in use in medical practice, the search for novel $\beta$-adrenoceptor blocking agents is still an actual problem. This is concerned with the fact that the majority of $\beta$-adrenoceptor blocking compounds has some disadvantages (their short-term efficacy, inhibiting effect on heart function, ability of giving rise to a number of side-effects of the central nervous system and the like). Of particular interest is the search for novel biologically active compounds having both $\beta$- and $\alpha$-adrenolytic activities because the presence of $\alpha$-adrenoblocking properties may favor the enhancement of their activity as hypotensive agents and the reduction of some disorders such as peripheral blood circulation failures (Raynaud's disease, Charcot's syndrome) which are associated with the indirect vasoconstrictive effect of $\beta$-adrenoceptor blocking compounds.

Known in the art is $\beta$-adrenoceptor blocking drug, namely propranolol used for prevention and treatment of heart ischemia, angina pectoris of effort, supraventricular arrhythmia, glaucoma and other cardiogenic or non-cardiogenic diseases. /Kay H. B., Angina pectoris, After nitrates and beta-blockers, what next?, Medical Progress, November , 1981 , 47-54; Mc Devitt D. G., Adrenoceptor blocking drugs: clinical pharmacology and therapeutic use, Drugs, 1979, 17, 267-288) .

Propranolol, however, is not suitable for arresting acute hypertensive crisis and has a low efficacy in heavy cases of hypertension, as well as in variable and labile angina pectoris and ominous ventricular arrhythmia. Propranolol may complicate the course of vasospastic cases of angina pectoris due to its indirect coronarocon-strictive effect.

Also known in the art is a medicinal agent, namely labetalol, specified by $\beta$- and $\alpha$-adrenoceptor blocking properties. /Louis W. J. , Mc. Neil J. J., Drummer O. H., Pharmacology of Combined $\alpha$-, $\beta$-blockade, Drugs, 1984, 28, suppl. 2,17-33/.

Labetalol, however, is only in use as antihypertensive agent and is not intended for application in heart ischemia, arrhythmias or glaucoma.

A pharmaceutical preparation of the invention with an antihypertensive, antianginal, antiarrhythmic and antiglaucomic effect is novel and it has not been described in literature.

BRIEF DESCRIPTION OF THE INVENTION

The main object of the present invention is to provide a pharmaceutical preparation with a pronounced $\beta$- and $\alpha$-adrenoceptor blocking activity, characterized by highly effective antihypertensive, antianginal, antiarrhythmic and antiglaucomic effects.

Another object of the present invention is to provide a pharmaceutical preparation having a low toxicity.

The main and other objects are accomplished by that a pharmaceutical preparation according to the invention consists of an active principle, namely 3-methyl-5-[2-(3-tert.butylamino-2-hydroxypropoxy) phenoxymethyl]-1,2,4-oxadiazole hydrochloride of the following formula:

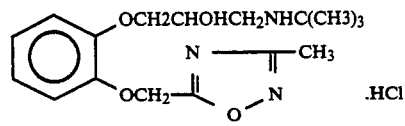

and a pharmaceutically acceptable diluent.

The preparation of the invention may be used in the form of tablets, injection solutions and eye drops.

As tablets, the pharmaceutical preparation of the invention contains an active principle preferably in an amount of 0.01 to 0.4 g per tablet; in the form of injection solutions it contains an active principle preferably in an amount of 0.1 or 1.0% by weight; in the form of eye drops the preparation contains an active principle preferably in an amount of 1.0 to 2.0 % by weight.

As pharmaceutical diluent, there may be used any pharmaceutically acceptable excipient for tablets or diluent for injection solutions and eye drops.

The preparation of the invention has $\beta$-adrenoceptor blocking activity in combination with an inhibiting effect on $\alpha$-adrenoceptors.

Reducing the effects of the sympathetic nervous system on cardiac $\beta$-adrenoceptors as well as vascular $\alpha$-adrenoceptors, the pharmaceutical preparation of the invention decreases the intensity and rate of heart beats, delays the atrioventricular conduction, via the atrioventricular node, lowers arterial pressure due to decreasing the cardiac output and the peripheral vascular resistance. The preparation of the invention has a non-specific membrane-stabilizing effect. The preparation of the invention shows an antihypertensive, antiischemic and antiarrhythmic properties. The preparation of the invention improves the myocardium blood supply. The bronchomotor tone due to blocking $\beta_2$-adrenoceptors by using the preparation of the invention increases. The preparation lowers intraocular pressure.

In $\beta$-adrenoceptor blocking activity the preparation of the invention is superior to the known medicinal agents, namely propranolol, oxprenolol and particularly labetalol; by duration of $\beta$-adrenoceptor blocking effect it is superior to propranolol and oxprenolol. As distinct from propranolol, oxprenolol and pindolol, the preparation of the invention shows a direct hypotensive and antihypertensive effect. The preparation of the invention is superior to labetalol by its hypotensive activity and duration of action and is distinguished from the latter by a coronarodilatating effect. The preparation of the invention is superior to propranolol, oxprenolol, pindolol and labetalol in antiarrhythmic activity.

The pharmaceutical preparation of the invention has a lower toxicity than propranolol, oxprenolol and pindolol.

DETAILED DESCRIPTION OF THE INVENTION

The active principle of the preparation according to the invention, namely 3-methyl-5-[2-(3-tert.butylamino-2-hydroxypropoxy)phenoxymethyl]-1,2,4-oxadiazole hydrochloride is a crystalline powder having from a creamy-white to creamy color, odorless, readily soluble in water, chloroform, ethanol and substantially insoluble in ethyl ether.

The active principle of the preparation of the invention may be prepared according to the conventional method by reacting pyrocatechol with chloromethyl derivative of 1,2,4-oxadiazole in the presence of a base in an organic diluent, such as acetone under reflux. The resulting oxy derivative of 5-phenoxymethyl-1,2,4-oxadiazole is reacted with epichlorohydrin, thereafter, the resulting epoxy-compound is subjected to react with excess of alkylamine in a low alcohol under reflux followed by recovering the base and converting it into its hydrochloride.

The active principle of the preparation according to the invention was tested in an animal experiment.

$\beta$-adrenoceptor blocking activity of the active principle of the pharmaceutical preparation of the invention was studied. The influence of the compound of the invention injected intravenously on isadrin's (isopropyl noradrenalin) positive chronotropic and depressor effects in the anesthetized rats was studied in a manner similar to that as described above in comparison with the known pharmaceutical preparations, namely propranolol, oxprenolol, pindolol and labetalol. The test substances were injected to several groups of animals (6-10 individuals each) in the graded doses of 0.001, 0.0025, 0.01, 0.025, and 0.1 mg/kg.

From the dosage of 0.0025 mg/kg the compound of the invention resulted in decreasing the heart rate (from 271±7 in the control to 249±11, 238±16, 204±14 and 181±14 beat/min. in the dosages of 0.0025, 0.01, 0.025, and 0.1 mg/kg, respectively). From the dosage of 0.1 mg/kg it gave rise to the lowering of arterial pressure (from 159±9 in the control to 141±11, 127±10 and 123±11 mm Hg in the dosages of 0.01, 0.025 and 0.1 mg/kg). From the dosage of 0.0025 mg/kg the compound of the invention gave rise to the dose-related suppression of the isadrin-initiated depressor effect (by 12,63, 82 and 90% in doses of 0.0025, 0.01, 0.025 and 0.1 mg/kg) and, starting from the dosage of 0.1 mg/kg, a positive chronotropic (by 25, 46 and 78% in doses of 0.01, 0.025 said 0.1 mg/kg, respectively) effect.

The test results are shown in Table 1.

TABLE 1

Influence of the Compound According to the Invention, Propranolol, Oxprenolol, Pindolol and Labetalol, Injected Intravenously, on Positive Chronotropic and Depressor Effects of Isadrin in the Anesthetized Rats

| NN | Substance (n-number of animals in a group) | Dosage inhibiting isadrin's positive chronotropism by 50%, ($ED_{50}$, mg/kg, i.v.) | Dosage inhibiting isadrin's depressor effect by 50% $ED_{50}$, mg/kg, i.v.) |
|---|---|---|---|
| 1. | Compound of the invention (n = 8) | 0.03 ± 0.001 | 0.008 ± 0.0007 |
| 2. | Propranolol (n = 6) | 0.42 ± 0.05 | 0.092 ± 0.025 |
| 3 | Oxprenolol (n = 6) | 0.26 ± 0.025 | 0.055 ± 0.005 |
| 4. | Pindolol (n = 5) | 0.025 ± 0.002 | 0.020 ± 0.002 |
| 5. | Labetalol (n = 6) | 0.700 ± 0.05 | 3.300 ± 0.2 |

The comparison of the $ED_{50}$ values showed that compound of the invention is superior to propranolol, oxprenolol and labetalol by a factor of 12; 9 and 23, respectively, by $\beta_1$-adrenoceptor blocking activity, and it is close to pindolol. By $\beta_2$-adrenoceptor blocking activity then compound of the invention is, respectively, 11; 4 412 and 2 times as high as propranolol, oxprenolol, labetalol and pindolol.

The effects of oral administration of the compound according to the invention as compared with the known drugs on the isadrin-initiated positive chronotropism in rats were tested.

The test results showed that by $\beta_1$-adrenoceptor blocking activity the compound of the invention when administered orally is superior to propranolol, oxprenolol and labetalol (by 14.8 and 35 times, respectively), but is inferior to pindolol.

The influence of intravenous injection of the compound according to the invention as compared with the known drugs on isadrin's positive chronotropic and depressor effects in the anesthetized cats was studied. The test results showed that by $\beta_1$-adrenoceptor blocking activity the compound according to the invention was superior to propranolol, oxprenolol and labetalol by a factor of 3.5; 35 and 550, respectively, and was close to pindolol. By $\beta_2$-adrenoceptor blocking activity the compound of the invention was, respectively, 2; 43 and 114 times as high as propranolol, oxprenolol and labetalol.

Thus, by $\beta$-adrenoceptor blocking activity the compound of the invention, when injected intravenously, is superior to propranolol, oxprenolol and labetalol in the anesthetized cats and rats.

The studies of $\beta$-adrenoceptor blocking effect duration of the compound according to the invention showed that by this value it was somewhat superior to propranolol and oxprenolol.

In studying the specificity of $\beta$-adrenoceptor blocking effect it has been found that compound according to the invention did not inhibit but even somewhat enhanced the positive inotropism of strophanthin, calcium chloride and theophylline while it completely arrested such effect of isadrin. Thus, the compound of the invention relates to specific $\beta$-adrenoceptor blocking agents.

$\beta$-adrenoceptor blocking activity of the compound according to the invention was studied.

The tests were carried out on male rats with body weight of 200-250 g which were anesthetized by using sodium pentobarbital (40–50 mg/kg, i.p.). The influence of intravenous injection of the compound according to the invention, oxprenolol and labetalol in a dosage of 3 and 10 mg/kg on the mesaton-initiated pressor effect (0.1 mg/kg, i.v.) was studied. The latter was injected 15 minutes before and 2 minutes after administration of β-adrenoceptor blocking agents. Altogether, 8 series of tests (4–5 animals each) were carried out. The compound of the invention, oxprenolol and labetalol, given in the dosage of 3 mg/kg, did not change the mesatone presser effect, but in the dosage of 10 mg/kg they suppressed it on the average by 76; 10 and 47%, respectively.

The same tests were carried out on cats.

The test results showed that in vivo the compound of the invention (in rats and cats) when injected intravenously did not differ from labetalol by β-adrenoceptor blocking activity.

As a result of such tests it has been found that the compound of the invention, like propranolol, fails to exhibit a partial agonistic activity, and, like propranolol and as distinct from labetalol and oxprenolol, has a non-specific membrane-stabilizing effect.

Hypotensive and antihypertensive properties of the compound according to the invention were also studied.

In experiments on cats with a body weight of 3–4 kg which were anesthetized by using urethane (1 g/kg) and alphachloralose (100 mg/kg, i.p.) the comparison of the effects of the compound according to the invention and labetalol, given in the graded doses (0.02; 0.1; 0.3; 1.0 and 5.0 mg/kg), on arterial pressure recorded in the common carotid artery by using electrical blood pressure gauge was carried out.

It has been found that the compound of the invention starting from the dosage of 0.02 mg/kg leads to the dose-related lowering of arterial pressure (from 163±8 in control to 147±12; 132±5; 96±7; 90±7 and 67±7 mm Hg in doses of 0.02; 0.1; 0.3; 1.0 and 5.0 mg/kg, respectively). The duration of hypotensive effect of the compound according to the invention taken in small dosages was of 5–30 minutes, but in large ones it was more than 3–4 hours. The same, but less pronounced and prolonged effect had labetalol as started from the dosage of 0.1 mg/kg. The comparison of $ED_{20}$ values showed that by hypotensive activity the compound of the invention was 9 times as high as labetalol.

The test results are given in Table 2.

TABLE 2

Comparison of Hypotensive Activity of the Compound According to the Invention and Labetalol Injected Intravenously in Anesthetized Cats

| NN | Active substance (n-number of animals) | Dose resulting in lowering of arterial pressure by 20%, $ED_{20}$ mg/kg, i.v. |
|---|---|---|
| 1 | Compound of the invention (n = 8) | 0.11 ± 0.01 |
| 2 | Labetalol (n = 7) | 1.0 ± 0.09 |

In the tests on conscious, normotensive rats 1 hour after administering the compound of the invention orally in a dosage of 10 and 50 mg/kg the arterial pressure lowering and a decrease in heart rate were noted while propranolol given in the dosage of 150 mg/kg had a small influence on arterial pressure and decreased the heart rate slightly. In the tests on the anesthetized, normotensive cats the compound of the invention injected intravenously showed a stronger hypotensive effect as compared with labetalol. In rats suffering from renovascular hypertension the compound of the invention in the dosage of 10 mg/kg (injected intramuscularly) lowered with confidence the arterial pressure (from 137±3 to 117±5 mm of Hg column) 30 minutes after being administered. The 2-week course of the administration of the compound according to the invention (10 mg/kg 1 time a day) caused the antihypertensive effect to be enhanced. By the end of the second week the arterial pressure was 110±8.6 mm Hg. Propranolol had a low efficacy under the same conditions.

Thus, the compound of the invention shows hypotensive and antihypertensive properties in normotensive cats and rats (administration i.v. and single per os), as well as in rats with a spontaneous and renovascular hypertension (single administration per os and the repeated injection i.m.) that distinguishes such compound from the conventional β-adrenoceptor blocking agents. When using the compound of the invention for a long time, its efficacy is not becoming low (no drug addiction).

An antiarrhythmic acivity of the compound according to the invention was studied.

In studying the effect of the compound according to the invention on the threshold of electrically induced ventricular fibrillation in the anesthetized cats it has been found that such compound, as well as propranolol, oxprenolol and labetalol given in the dosage of 1 mg/kg did not change, but increased considerably this threshold administered in the amount of 5 mg/kg. Moreover, the value of increasing such threshold was higher for the compound of the invention and labetalol as compared with propranolol and oxprenolol. Pindolol had no effect on the threshold of electrically induced ventricular fibrillation in dosages tested.

The comparative studies of the effect of the compound according to the invention, propranolol, oxprenolol and labetalol on strophantin G-induced arrhytmia in guinea-pigs showed that the compound of the invention (0.1–3.0 mg/kg, i.v.) gave rise to the dose-related increase of arrhythmogenic and lethal doses of strophantin, with its antiarrhythmic activity and efficacy being superior to propranolol, oxprenolol and labetalol.

The test results are given in Table 3.

TABLE 3

Effects of the Compound of the Invention, Propranolol, and Labetalol on Cardiotoxic Action of Strophantin in Guinea Pigs

| Preparation | Dosage mg/kg, i.v. | Number of animals | Arrhythmogenic and lethal doses of strophantin as compared with control (%) | | |
|---|---|---|---|---|---|
| | | | extra-systoles | ventricular fibrillation | animal death |
| 1 | 2 | 3 | 4 | 5 | 6 |
| Control | | 25 | 100 (95–105) | 100 (95–104) | 100 (95–105) |
| Compound of the invention | 0.1 | 5 | 118 (105–131) | 115.6 (108–123) | 118.7 (111–127) |
| | 0.3 | 5 | 125.9 (120–131) | 113.1 (107–119) | 123.5 (106–120.8) |
| | 1.0 | 5 | 148.2 (138–158) | 147.2 (142–157) | 142.6 (138–147) |
| | 3.0 | 5 | 157.0 (133–171) | 170.2 (160–180) | 150.7 (142–159) |
| Propranolol | 0.3 | 5 | 92.7 (90–96) | 97.9 (89–102) | 94.3 (92–97) |
| | 1.0 | 5 | 110 | 106.3 | 104.3 |

TABLE 3-continued

Effects of the Compound of the Invention, Propranolol, and Labetalol on Cardiotoxic Action of Strophantin in Guinea Pigs

| Preparation | Dosage mg/kg, i.v. | Number of animals | Arrhythmogenic and lethal doses of strophantin as compared with control (%) | | |
|---|---|---|---|---|---|
| | | | extra-systoles | ventricular fibrillation | animal death |
| 1 | 2 | 3 | 4 | 5 | 6 |
| | | | (103–117) | (101.3–113) | (101–108) |
| | 3.0 | 5 | 119 (116–122) | 120 (95–133) | 119 (98–129) |
| Labetalol | 0.3 | 5 | 101 (92–10) | 113 (108–118) | 103 (101–106) |
| | 1.0 | 5 | 127 (123–131) | 131 (127–134) | 128 (125–131) |
| Labetalol | 3.0 | 5 | 136 (130–143) | 137 (129–144) | 132 (120–138) |
| Oxprenolol | 0.3 | 5 | 105 (90–120) | 101 (95–107) | 102 (99–105) |
| | 1.0 | 5 | 120 (111–129) | 110 (100–120) | 112 (107–117) |
| | 3.0 | 5 | 110 (105–116) | 121 (116–126) | 112 (110–114) |

The compound of the invention injected intravenously in the dosage of 1 mg/kg prevented the ventricular fibrillation in case of temprorary occlusion of the left descending coronary artery in 2 from 4 of the anesthetized dogs with the drived rhythm and complete AV block. Propranolol had the same effect.

The test results are given in Table 4.

TABLE 4

Effects of the Compound According to the Invention on Ventricular Fibrillation Rate During Acute Occlusion and Reperfusion

| Test NN | Before injection | 10 min after injection | 60 min after injection |
|---|---|---|---|
| 1 | 2 | 3 | 4 |
| *Compound of the Invention* | | | |
| 1 | — | — | — |
| 2 | — | — | — |
| 3 | — | — | — |
| 4 | O | — | — |
| 5 | O | O | O |
| 6 | R | — | — |
| 7 | R | R | R |
| *Propranolol* | | | |
| 1 | — | — | — |
| 2 | — | — | — |
| 3 | R | R | R |
| 4 | R | R | — |
| 5 | O | — | — |
| 6 | O | O | R |

Symbols to be accepted:
O—ventricular fibrillation occured during coronary occlusion;
R—ventricular fibrillation occured during reperfusion;
"—" no ventricular fibrillation In the anesthetized rats the compound of the invention injected intravenously in the dosage of 0.1 mg/kg resulted in dilatation (with confidence) of coronary vessels, both in the whole myocardium and its subendocardial layers followed by the development of myocardial perfusion, as well as in its most ischemia-sensitive subendocardial layers. The coronarodilative effect of the compound according to the invention is not associated with its $\beta$- and $\alpha$-adrenoceptor blocking activity and its influence on the systemic perfusion pressure and pump function of the heart. Under the same conditions labetalol did not lead to the dilatation of coronary vessels, and propranolol had an unfavourable effect on transmural, myocardial perfusion.

In the anesthetized rats with acute labile coronary occlusion the compound of the invention injected intravenously in the dosage of 5 mg/kg resulted in decreasing in the aortic ventricle necrosis in mass and size. Propranolol has a similar effect.

The test results are given in Table 5.

TABLE 5

Effects of the Compound of the Invention and Propranolol on Size and Mass of Myocardium Necrosis in Rats with Labile Coronary Occlusion

| Preparation | Dosage, mg/kg | The number of tests | Area of myocardium necrosis (% to the total area of aortic ventricle) | Mass and size of myocardium (% to the total area of aortic ventricle) |
|---|---|---|---|---|
| Control | — | 14 | 33.5 ± 2.5 | 31.2 ± 1.96 |
| Compound of the invention | 1 | 6 | 30 | 31.5 |
| Compound of the invention | 5 | 16 | 24.3 ± 3.4$^x$ | 23.6 ± 3.2$^x$ |
| Propranolol | 5 | 10 | 23 ± 4.05$^x$ | 24.8 ± 2.9$^x$ |

$^x$P < 0.05

Using the labeled microsphere method, a comparative study of the effects of the preparation according to the invention and labetalol in dosages which give rise to effective blocking of $\beta$- and $\alpha$-adrenoceptors on cardiac output and its distribution between essential vascular regions in the anesthetized normotensive rats, and the corresponding effects of the compound of the invention in the anesthetized rats with persistent renovascular hypertension was conducted. The test results showed that the preparation of the invention used in $\beta$-adrenoceptor blocking doses, like labetalol, exhibits vasodilating properties in normotensive rats. However, if the most sensible to the preparation of the invention are pulmonary, testicular, and particularly cardiac blood vessels, then to labetalol-the vessels of skeletal muscles, testicles, spleen, kidneys and adrenals. In using dosages to block $\alpha$-adrenoceptors, the nature of vasodilating effect of the preparation of the invention is becoming low-selective as compared with a slight change of vasodilating nature of labetalol.

In rats with renovascular hypertension, as well as in normotensive rats, the preparation of the invention, like labetalol, shows vasodilating properties.

The effects of the compound according to the invention on intraocular tension and hydrodynamics of the eye was tested in 28 chinchilla rabbits with body weight of 2.5–3.5 kg.

The effects of solutions of the compound according o the invention in comparison with propranolol on the status of anterior segment of eyeball, pupil width, intraocular tension of intact eyes, eye hydrodynamics, as well as on the course of prostaglandin-associated hypertension of the eye-were studied.

In all the tests, the right animal eyes were experimental wherein different concentrations of solutions of the compound according to the invention and propranolol were twice instilled in 2 drops with an interval of 1–2 minutes. The left animal eyes were control wherein using the same procedure a diluent was instilled.

The solutions of the compound according to the invention of all the tested concentrations (0.5, 1 and 2% solutions) are well-tolerable for rabbit eyes, have no irritating effect, do not change considerably the pupil value and significantly lower intraocular tension of intact rabbit eyes for 6–8 h due to the decrease in secretion of surface water (watery moisture) (propranolol action was continued for 4 hours). The test results are given in Table 6.

TABLE 6
Effect of 1% Solution of the Compound of the Invention and Propranolol on Intraocular Tension of Intact Rabbit Eyes

| NN | Experimental time | Number of tests | Intraocular tension level M ± m OD | OS | P | Average decrease of intraocular tension OD M ± m |
|---|---|---|---|---|---|---|
| 1 | 2 | 3 | 4 | 5 | 6 | 7 |
| | | | Compound of the Invention | | | |
| 1 | Background | 8 | 19.3 ± 0.6 | 19.2 ± 0.5 | — | |
| 2 | 1 hour | 2 | 17.1 ± 0.3 | 19.0 ± 0.6 | <0.05 | 1.9 ± 0.3 |
| 3 | 2 hours | 8 | 16.5 ± 0.4 | 19.1 ± 0.7 | <0.01 | 2.6 ± 0.2 |
| 4 | 3 hours | 8 | 17.1 ± 0.4 | 19.4 ± 0.7 | <0.01 | 2.3 ± 0.3 |
| 5 | 4 hours | 8 | 17.1 ± 0.2 | 19.4 ± 0.5 | <0.01 | 2.3 ± 0.3 |
| 6 | 5 hours | 8 | 17.6 ± 0.4 | 19.1 ± 0.6 | <0.05 | 1.5 ± 0.5 |
| 7 | 6 hours | 8 | 17.8 ± 0.4 | 19.0 ± 0.3 | <0.05 | 1.2 ± 0.4 |
| 8 | 24 hours | 8 | 18.2 ± 0.7 | 19.0 ± 0.9 | >0.5 | 0.8 ± 0.5 |
| | | | Propranolol | | | |
| 9 | Background | 9 | 20.1 ± 0.4 | 20.1 ± 0.5 | — | — |
| 10 | 1 hour | 9 | 19.1 ± 0.4 | 21.5 ± 0.5 | <0.01 | 2.4 ± 0.4 |
| 11 | 2 hours | 9 | 17.8 ± 0.4 | 20.4 ± 0.4 | <0.01 | 2.6 ± 0.3 |
| 12 | 3 hours | 9 | 18.0 ± 0.5 | 20.4 ± 0.5 | <0.01 | 2.4 ± 0.3 |
| 13 | 4 hours | 9 | 18.4 ± 0.7 | 20.6 ± 0.7 | <0.05 | 2.2 ± 0.2 |

Symbols to be accepted:
M—mean arithmetic value (ram of Hg column);
m—standard error of mean arithmetic value;
P—confidence criterion;
OD—right eye under test;
OS—left eye under control.

In experiments on male albino mice with body weight of 16–17 g, acute toxicity of the compound according to the invention in comparison with that of propranolol, oxprenolol, pindolol and labetalol was studied by intravenous and oral administrations. $LD_{50}$ values were estimated by using the Litchfield-Wilckoxon method. The animal health status and behavior were observed for 3 days. The experimental results are given in Table 7.

TABLE 7
Acute Toxicity of the Compound According to the Invention, Propranolol, Oxprenolol, Pindolol and Labetalol in Albino Mice

| NN | Substance | $LD_{50}$, i.v. injection, mg/kg | $LD_{50}$, oral administration, mg/kg |
|---|---|---|---|
| 1 | Compound of the invention | 72.5 | 600.0 |
| 2 | Propranolol | 28.1 | 315.0 |
| 3 | Oxprenolol | 20.0 | 375.0 |
| 4 | Pindolol | 29.0 | — |
| 5 | Labetalol | 97.5 | 660.0 |

As seen from Table 7, the compound of the invention when administered intravenously has a lower toxicity (2–4 times as low as compared with propranolol, oxprenolol and pindolol and does not differ from labetalol. When administered orally, the compound of the invention is less toxic (2–3 times) than propranolol and oxprenolol and does not differ considerably in toxicity from labetalol.

Studying the chronic toxicity of the compound according to the invention when administering in intragastrically showed an excellent tolerance of experimental animals to the preparation.

The compound of the invention when administering it intragastrically in a dosage of 5 and 30 mg/kg for 6 months, that is 1/120 and 1/20 of $LD_{50}$, but exceeds the presumable daily dose by a factor of 2 and 15, respectively, not exert an essential influence on behavior, appearance, the most important body functions. Moreover, it did not change the clinical blood values (hemoglobin content, red cell number, white cell number, leukocyte count and platelet number), had no effect on biochemical blood values, did not lead to pathologic alterations in structure of internals and did not exert any locally irritant effect.

Thus, the active principle of the preparation according to the invention, 3-methyl-5-[-2-(3-tert.butylamino-2-hydroxypropoxy)phenoxymethyl]-1,2,4-oxadiazole hydrochloride is a highly effective $\beta$-adrenoceptor blocking agent simultaneously having $\alpha$-adrenoceptor blocking and vasodilator activities. The compound of the invention shows an antihypertensive, antiischemic and antiarrhythmic effect. The compound of the invention is close to labetalol by pharmacologic spectrum. It is close to the conventional $\beta$-adrenoceptor blocking agents, namely propranolol, oxprenolol and pindolol by its effect. As compared with the known $\beta$-adrenoceptor blocking agents the compound according to the invention has some positive features:

by adrenoceptor blocking activity in vivo, when using different ways of administration, it is superior to propranolol, oxprenolol, and particularly labetalol;
  by $\beta$-adrenoceptor blocking effect duration, it is superior to propranolol and oxprenolol;
  as distinct from propranolol, oxprenolol and pindolol, it shows under experiment a direct hypotensive and antihypertensive action and particularly, it is superior to labetalol by hypotensive activity and duration of such effect;
  it differs from labetalol by a direct coronarodilating effect;

by antiarrhythmic activity and efficacy (influence on the threshold of electrically-induced ventricular fibrillation and strophanthin-related arrhythmia) it is superior to propranolol, oxprenolol, pindolol and labetalol.

In experimental conditions the compound of the invention leads to the pronounced decrease in intraocular tension. As compared with propranolol, oxprenolol and pindolol, the compound according to the invention is less toxic when injecting it fastly intravenously or administering it per os.

The preparation of the invention was clinically tested in patients.

In the open clinical experiment hypotensive activity of the preparation of the invention was studied in 38 patients in the age of 37 to 70 years suffering from arterial hypertension of different severity and an antianginal effect was tested in 12 patients of 45-59 years old with heart ischemia, as well as cardiac angina of effort of the I-III functional class. In the patients under test with arrhythmia, an antiarrhythmic action of the preparation according to the invention was determined.

Not included into such experiment were patients with circulatory deficiency, bradicardia (heart rate less than 50 beats per rain), atrioventricular conduction disorders, bronchoobstruction syndrome.

In testing the preparation of the invention clinically, the following methods were used: measurement of arterial tension by the Korotkov procedure (in reclining position, 3 times in 1 minute), electrocardiography in the conventional 12 derivations, electrocardiographic monitoring, the pair veloergometric tests followed by taking an electrocardiogram and controlling arterial tension. The parameters of the central hemodynamics were measured using a blood-flow meter by impulse dopplerography with suprasternal access with computer-processing of the curves.

The injection dosage form of the preparation according to the invention was studied in the acute drug test on 12 patients having a high arterial tension. 1-2 ml of a 1% solution of the preparation of the invention dissolved in 10 ml of a 0.9% aqueous solution of sodium chloride were injected to the patients. The dynamics of arterial tension and heart rate were determined on the $1^{st}$, $10^{th}$, $15^{th}$, $30^{th}$ and $60^{th}$ minutes after injection of the preparation, and then, in every hour to return it to the initial values. The lowering of arterial tension was noted immediately after completion of injecting the preparation to attain the maximum effect by the 10-15 and 60 minutes, with systolic pressure decreased, on the average, from 208.75 to 170.17 mm of Hg column that was 18.5%, diastolic pressure lowered from 109.17 to 95 mm of Hg, i.e. by 13.5% and the mean dynamic pressure—from 142.37 to 121.51 mm of Hg column, i.e. by 14.7%. The heart rate decreased from 80 to 65 beats per min, that was 18.8%. The duration of hypotensive effect in most of the patients was 3-4 hours. In 2 patients (16.7%) such effect has not been accomplished.

In employing the preparation according to the invention in the form of tablets along with studying the effects of the preparation on arterial pressure and heart rate, there were determined the alterations of the central hemodynamics values. Depending on the initial values, all the patients were divided into 2 groups: the first group involved 18 patients with hyperkinetic type of hemodynamics and the second—14 patients with eu- and hypokinetic types.

In the acute drug test the preparation of the invention was administered in the dosage of 10-40 mg, depending on the values of arterial tension and heart rate and hypotensor resistivity. The hypotensive effect became to manifest itself to the $45^{th}$-$60^{th}$ minutes and it had the maximum value by the 90-120 minutes. Such effect remained up to 4-6 hours after administration of the preparation and decreased considerably to the $8^{th}$ hour. In the period of the maximum hypotensive effect in the patients of the first group the systolic arterial tension was lowered by 12.8%, diastolic pressure—by 12.5% mean-dynamic arterial tension by 12.6%. The heart rate decreased by 13.4%. Moreover, the cardiac output decreased by 24.8%, and the common peripheral resistance increased by 14.2%. In the second group such values were changed as follows: systolic arterial tension became lower by 12.7%, diastolic pressure by 12.4%, mean-dynamic arterial tension—by 12.5%, heart rate decreased by 6.9%, with the cardiac output increased by 12.4%, and the common peripheral resistance was lowered by 16.8%.

The course of therapy with the preparation according to the invention was conducted in 14 patients of the first group, and in 12 patients of the second one. The preparation was administered in a dosage of 30-120 mg a day divided in 3 doses. The dosage was determined by the initial values of hemodynamics and the results obtained during the acute drug test.

On the 3-$4^{th}$ week of the course of monotherapy there were obtained the following values: in the first group the systolic pressure became lower by 16.8%, diastolic pressure by 13.9% and mean-dynamic arterial tension by 15.6%. The heart rate decreased by 15.7%. Moreover, the cardiac output decreased by 21.7%, and the peripheral vascular resistance decreased by 9.5%. In the second group, the systolic pressure decreased by 17%, the dyastolic arterial pressure lowered by 14.1%, mean-dynamic arterial pressure by 15.4%. The heart rate decreased by 4.1%, the cardiac output increased by 4.7% and the peripheral resistance became lower by 18.2%.

The recurrence of the hypotensive effect absence in groups was approximately the same and was about 20%.

Some of the patients receiving the preparation according to the invention at the time of their stay in hospital were under routine examination. The considerable changes in the general blood and urine tests were not noted. In the majority of the patients there were observed the improvement of the general state, disappearance or reduction of headaches and cardiac discomfort.

Such investigation showed the presence of the hypotensive effect of the preparation in patients suffering from arterial hypertension with different types of hemodynamics.

In 10 of 12 patients with cardiac ischemia, angina of effort of the I-III functional class, a positive clinical effect (83.3%) was observed. Moreover, the lowering of the recurrence of anginal attacks, the reduction of the need in nitroglycerol, the positive dynamics in electrocardiogram were noted.

Another placebo-controlled investigation of a hypotensive and antianginal effect of the preparation according to the invention was conducted on 18 male patients at the age of 47-58 suffering from cardiac ischemia and persistent angina of stress of the II and the III funcitonal classes and on 18 patients aged of 34-63 with hypertension of the I and the II phases.

At the first stage of the study in 8 patients suffering from heart ischemia there was evaluated their tolerance to the single administration of the preparation according to the invention in the following dosages: 10 mg in 4, 20 mg in 2, and 40 mg in 2 human beings. Along with studying the drug tolerance in all the patients there were conducted pharmacodynamic tests at the state of rest characterized by measuring the heart rate and arterial tension before administration of the preparation and 1, 2, 3, 4, 5 and 24 hours after taking a single dose. At the second stage of the study, in 10 patients there were conducted the tests using tredmile with placebo and a single dose of the preparation according to the invention (3 humans per 40 ml and 7 ones per 80 mg). At the third stage the comparison of the effects of the preparation according to the invention and propranolol, taken in the amount of 80 mg each, was conducted by using pharmacodynamic tests on tredmile in 7 patients. Such pharmacodynamic tests were characterized by carrying out the individually chosen tredmile loadings before and 0.5, 2 and 6 hours after administration of the preparation or placebo. The criterion of ceasing all the loading tests served a moderate anginal attack.

The pharmacodynamic tests at rest showed that in all 8 patients the preparation according to the invention resulted in decreasing the heart rate during 5 hours after administration of its single dose. The beginning of chronotropic effect was recorded 1 hour after administration of the preparation, with the decrease of heart rate in different patients being of 6 to 18 beats per min. In 6 of 8 patients the decrease in heart rate was of 10 beats and more. The most negative chronotropic effect was recorded 2 and 3 hours after administration of the preparation (by 15 beats per min on the average). In 5 hours after administration of a single dose the negative chronotropism remained sufficiently pronounced (decrease in heart rate by 10 beats and more was observed in 5 out of 8 patients). In 24 hours the chronotropic effect failed to be observed.

In this group of patients the dependence of the degree of decreasing the heart rate at rest on the employed single dose of the preparation has not been discovered.

Thus, the manifestation of the negative chronotropic effect of the preparation according to the invention at rest substantially was determined by the initial value of heart rate and patient's peculiarities, and not the employed single dose of such preparation.

The lowering of systolic pressure at rest by 20 mm of Hg column and more was noted in 4 patients. The hypotensive effect remained for 5 hours. The considerable changes of diastolic pressure at rest have not been discovered.

Mean group and individual data concerning the effect of the preparation according to the invention on the loading duration to the occurence of an anginal attack are indicative of the valid increase in duration of the loading made by the patients with a persistent angina of effort. An antianginal effect of the preparation according to the invention manifests itself 0.5 hour after administration and lasts, on the average, not less than 6 hours.

In comparing the preparation of the invention and propranolol in 7 patients, there was discovered a more pronounced effect of the former on the loading duration, but the valid differences between them 0.5, 2 and 6 hours after administration were not noted.

The preparation of the invention had a more pronounced effect on the duration of the loading in comparison with propranolol, mainly, on account of the quick manifestation of the effect.

The study of the influence of the preparation according to the invention on the change of the ST-segment depression in comparison with placebo and propranolol showed that it had a pronounced effect on such depression, both at rest and under loading. An antiischemic action of the preparation according to the invention somewhat exceeded such an effect of propranolol in comparing the same single doses of them.

The analysis of side-effects of the preparation according to the invention showed that, on the whole, the tolerance of patients was sufficiently good. However, in some patients a subtle headache, giddiness, sleepiness and dryness in the mouth were observed.

The studies of an antihypertensive effect of the preparation involved two sections as follows: 1. the acute pharmacodynamic test in comparison with placebo; 2. a short-term course of treating patients with arterial hypertension in hospital for 2 weeks.

The pharmacodynamic tests were conducted in 13 patients. In total, there were carried out 29 pharamcodynamic tests, out of them with 10 mg the preparation according to the invention in 6 cases, 20 mg in the 7, 30 mg in the 4 and with placebo in 8 tests.

In administering 40 mg of the preparation accoring to the invention, there was discovered the valid decrease in systolic pressure (from $148.5\pm8.34$ to $132.5\pm9.78$ mm of Hg, $p<0.01$) in 1 hour, and the valid lowering of diastolic pressure (from $104.5\pm4.5$ to $91.5\pm5.12$ mm of Hg, $p<0.05$) in 5 hours.

It should be also noted that most of the systolic and diastolic pressure values after administration of the preparation according to the invention were lower than the initial level (although not to be valid) while the values of systolic and diastolic pressure after administration of placebo were on the initial level or unreliably high.

The pharmacodynamic tests at reclining position did not show any significant variations in the values of systolic and diastolic pressure when using various dosages of the preparation according to the invention.

When administering 10 and 30 mg of the preparation according to the invention, systolic pressure at standing validly lowered only in 30 and 60 minutes, respectively. In other points the valid lowering of systolic pressure was not noted. At the same time in the pharmacodynamic tests using 20 mg of the preparation according to the invention systolic pressure validly lowered in all the points during 3 hours, and in administering 40 mg of the preparation it lowered in all the points for 5 hours.

Diastolic pressure at standing, when using 10, 20 and 30 mg of the preparation according to the invention, validly remained unchanged, and it significantly lowered only at the first point in an hour after administration of the preparation (from $114.0\pm5.6$ to $105\pm6.24$; $p<0.05$) when employing 40 mg of the preparation.

The heart rate validly decreased in all points for 5 hours by using 10, 20 and 30 mg the preparation according to the invention and at the dosage of 40 mg it significantly lowered for 2 hours.

Due to the fact that in the pharmacodynamic tests of the preparation according to the invention at reclining position no significant variations of the systolic and diastolic pressure values had been discovered while a valid decrease in systolic pressure in using various dosages of the preparation, and especially 20 and 40 mg had been observed at standing, there was conducted a special test for hypotension manifestation at orthostatic position. It has been found that the hypotensive effect of the preparation at orthostatic position on systolic pressure manifested itself invalidly, rises as the dosage of the preparation is increased and becomes valid 2 hours after administrating 40 mg of the preparation (with attaining Δ% 14.3; p<0.05). The lowering of diastolic pressure at orthostatic position is less pronounced. In conducting the pharmacodynamic tests of the preparation according to the invention clinical signs of postural hypotension have not been discovered.

Side effects were noted in 3 (23.1%) of 13 patients which were under pharmacodynamic tests. In 1 patient a slight giddiness was noted by changing the body into orthostatic position (without lowering arterial tension) when administering 40 mg of the preparation according to the invention. In patient the feeling of heat in face occurred 30 minutes after administration of 30 mg of the prepration according to the invention (without changing arterial tension). In 1 patient some discomfort occurred in the breast when administering 10 mg of the preparation according to the invention.

A short-term course of treatment for 2 weeks in hospital was conducted in 5 patients suffering from arterial hypertension. The dosage of the preparation was of 80 to 240 mg a day (on the average of 144.0±22.1 mg) by the end of the first week, and by the end of the second week it also was 80-240 mg per day (average 152.0±26.5 mg).

In 2 of 5 patients the complete hypotensive effect was noted by the end of the first week while it was absent in the other patients. By the end of the second week such effect was noted in 4 of 5 patients, the effect was complete in 3 patients, partial in 1 patient and 1 patient revealed no effect.

The results of the 24-hour monitoring of arterial tension in the course treatment using the preparation according to the invention indicate that as long as by the end of the first week a hypotensive effect takes place to show the lowering of the mean-day value of systolic pressure (invalidly), the valid lowering of the mean-day value of diastolic pressure, the valid decrease in resulting amplitude of systolic pressure and in hyperbarical action of diastolic pressure.

By the end of the second week the hypotensive effect enhances by showing the decrease in all the values being studied. The valid decrease in mean-day values of systolic and diastolic pressure, heart rate, resulting amplitude and hyperbarical effect of systolic pressure as well as the total action of hyperbarism is noted. Moreover, the invalid decrease in resulting amplitude of diastolic pressure, resulting amplitude of heart rate and hyberbarical diastolic pressure effect becomes apparent.

The side effect was noted in 1 patient (skin itch). This, however, was not strong and did not cause the treatment to be cancelled.

Orthostatic hypotensive reactions in the course treatment were not noted.

The preparation of the invention was clinically tested as antiglaucomic agent.

The preparation of the invention was tested on 128 patients affected with the primary open-angle glaucoma at the early or developed stages of such disease characterized by the moderately increased or high intraocular pressure. In 87% of patients a single instillation of a 1% solution of the preparation according to the invention resulted in the pronounced lowering of intraocular tension. The effect of the preparation according to the invention manifested itself 15 minutes after instillation of the preparation (the lowering of intraocular pressure was on the average 3.8 mm of Hg column), attained the maximum value in 4-6 hours (7.2-7.4 mm of Hg column) and lasted 24 hours above (4.4 mm of Hg column), with the systemic arterial tension substantially being unchanged (the maximum lowering of systolic and diastolic pressure 4 hours after instillation was 5 and 3 mm of Hg column, respectively). In all patients given the instillation of a 1% solution of the preparation according to the invention systematically by 1 drop twice a day within 1 week to 10 months a valid decrease in intraocular tension was noted.

The use of a 1% solution of the preparation according to the invention caused no eye discomfort in patients.

The preparation of the invention was tested on 108 patients with different cases of glaucoma resistant to the conventional antiglaucomic therapy. In instilling a 1 solution of the preparation according to the invention 2-3 times a day for 1 week of treatment the lowering of intraocular pressure more than by 2 mm Hg was attained in 94% of patients, and its resetting (less than 22 mm Hg) was observed in 50 patients. A long-term resetting for more than 1 month of intraocular tension was attained in 76% of patients. In 7 patients a hypotensive effect was absent or proved to be unstable that required to use the instillation of a 2% solution of the preparation according to the invention, with intraocular pressure being reset (lowering of intraocular tension from 24.2 to 21.3 mm of Hg column) in 4 of 7 patients.

A hypotensive effect of the preparation according to the invention, like thymolol, was associated not only with inhibition of intraocular liquid secretion, but with improvement of its outflow.

The tolerance of patients to the preparation according to the invention was good. The local side effects including allergic reactions were not noted. The pupil width substantially remained unchanged, and only in 5 cases a moderate dilatation of it by 0.5-1.0 mm was noted. As to the systemic effects, in 2 patients a moderate bradicardia and a slight lowering of the general arterial tension were noted. The vision acuity remained unchanged. The visual field remained unchanged in most cases, although in some patients it became somewhat broaden. On the basis of test results one may come to conclusion of a high antiglaucomic acivity of the preparation according to the invention, and good tolerance of an organism to it.

The antihypertensive, antianginal, antiarrhythmic and antiglaucomic pharmaceutical preparation of the invention may be used in various dosage forms (tablets, injection solutions, eye drops). The dosage forms are prepared by the conventional methods.

The preparation of the invention is employed in tablets by 0.01 and 0.04 g, in ampoules by 5 ml of a 0.1% or 1% solution of an active principle. Eye drops are employed as a 1 or 2% solution of an active principle. As the excipient for a tablet and the diluent for an injection solution and eye drops any pharmaceutically acceptable excipient or diluent may be used.

In cardiologic practice the preparation according to the invention is administered per os or injected intravenously.

In occurring hypertensive crises 1-2 ml of a 1% solution of the preparation are injected for 1 minute. The dosage of the preparation is, if required, repeated with intervals of 5 minutes up to the occurrence of the effect. In total, there is injected not more than 5-10 ml of a 1% solution of the preparation.

In case of a long-term antihypertensive therapy, the preparation of the invention is administered in tablets starting from the dosage of 0.01 g (10 mg) 2-3 times a day. If the tolerance is good, the dosage is gradually increased (when necessary) by 10-20 mg a day to a daily dose of 80-120 mg.

For arresting cardiac rhythm disorders and anginal attacks, the preparation of the invention is injected intravenously in the amount of 1 ml of a 0.1% solution (1 mg) for 1 minute, and then, the dosage is reinjected with intervals of 2 minute. The cumulative dose should not be in excess of 5 ml of a 0.1% solution (5 mg).

For supporting antianginal and antiarrhythmic therapy the preparation according to the invention is prescribed in tablets to start from the dosage of 0.01 g (10 mg) 2-3 times a day. If being well tolerable, the dosage is gradually increased (when necessary) by 10-20 mg a day to a daily dose of 80-120 mg.

The preparation of the invention is usable as eye drops. (a 1 or 2% solution of an active principle). Eye drops are used by instillating them into the conjunctival sac (by 2 drops twice a day).

The preparation according to the invention generally is well tolerable. In some cases, the deceleration of heart rate and the lowering of the systemic arterial tension (resorption effect) may occur.

We claim:

1. A pharmaceutical preparation having antihypertensive, antianginal, antiarrhythmic and antiglaucomic effect, comprising an active principle, which is 3-methyl-5-[2-(3-tert.butylamino-2-hydroxypropoxy)phenoxymethyl]-1,2,4-oxadiazole hydrochloride of the following formula:

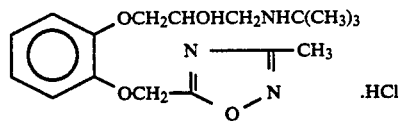

and a pharmaceutically acceptable diluent.

2. A pharmaceutical preparation according to claim 1 in the form of tablets comprising an active principle in the amount of 0.01-0.04 g per 1 tablet.

3. A pharmaceutical preparation according to claim 1 in the form of an injection solution comprising an active principle in the amount of 0.1 and 1.0% by weight.

4. A pharmaceutical preparation according to claim 1 in the form of eye drops comprising an active principle in the amount of 1.0 to 2.0 % by weight.

5. A pharmaceutical preparation according to claim 1 for antianginal and antiarrhythmic effect, wherein the dosage is 80 to 120 mg per day.

6. A pharmaceutical preparation according to claim 1 for treating arterial hypertension, wherein the dosage is 80 to 240 mg per day.

* * * * *